US008299258B2

(12) United States Patent
Buenger et al.

(10) Patent No.: US 8,299,258 B2
(45) Date of Patent: Oct. 30, 2012

(54) METHOD OF MAKING PIPERIDINE DERIVATIVES

(75) Inventors: Greg S. Buenger, Charles City, IA (US); Paul A. Jass, Charles City, IA (US); Kezia Peixoto Schutz, Charles City, IA (US)

(73) Assignee: Cambrex Charles City, Charles City, IA (US)

( * ) Notice: Subject to any disclaimer, the term of this patent is extended or adjusted under 35 U.S.C. 154(b) by 205 days.

(21) Appl. No.: 12/612,089

(22) Filed: Nov. 4, 2009

(65) Prior Publication Data

US 2010/0137604 A1 Jun. 3, 2010

Related U.S. Application Data

(60) Provisional application No. 61/111,118, filed on Nov. 4, 2008.

(51) Int. Cl.
| | |
|---|---|
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |
| C07D 211/56 | (2006.01) |
| C07D 211/92 | (2006.01) |
| A61K 31/445 | (2006.01) |

(52) U.S. Cl. ........ 546/213; 546/224; 546/210; 514/326; 514/329

(58) Field of Classification Search ........................ None
See application file for complete search history.

(56) References Cited

U.S. PATENT DOCUMENTS

| | | | |
|---|---|---|---|
| 3,998,834 A | 12/1976 | Janssen et al. | |
| 4,179,569 A | 12/1979 | Janssen et al. | |
| 5,019,583 A | 5/1991 | Feldman et al. | |
| 5,489,689 A | 2/1996 | Mathew | |
| 7,074,935 B2 * | 7/2006 | Mathew et al. | 546/210 |
| 7,208,604 B2 | 4/2007 | Mathew et al. | |
| 2006/0149071 A1 | 7/2006 | Mathew et al. | |

FOREIGN PATENT DOCUMENTS

| | | |
|---|---|---|
| WO | 01/40184 A2 | 6/2001 |
| WO | 2004/108636 A2 | 12/2004 |
| WO | 2008-005423 A1 | 1/2008 |
| WO | 2008/045192 A2 | 4/2008 |

OTHER PUBLICATIONS

Carey, FA. et al. Advanced Organic Chemistry: Structure and mechanisms. 2007, p. 413-414, table 4.6.*
Carey, FA. Advanced Organic Chemistry: Structure and Mechanisms. 2007, p. 413-414, table 4.6.*
Paul L. Feldman and Marcus F. Brackeen, A Novel Route to the 4-Anilido-4-(Methoxycarbony) Piperidine Class of Analgetics, The Journal of Organic Chemistry, Jun. 22, 1990, pp. 4207-4209, vol. 55, No. 13, The American Chemical Society, U.S.A.
Douglass F. Taber and Mohammad Rahimizadeh, Amide to Ester Conversion: A Practical Route to the Carfentanil Class of Analgetics, The Journal of Organic Chemistry, Jul. 3, 1992, pp. 4037-4038, vol. 57, No. 14, The American Chemical Society, U.S.A.
John A. Colapret et al., Synthesis and Pharmacological Evaluation of 4,4-Disubstituted Piperidines; Journal of Medical Chemistry, Jun. 6, 1988, pp. 968-974, vol. 32, 1989, The American Chemical Society, U.S.A.
Willem F.M. Van Bever et al, Synthetic Analgesics. Synthesis and Pharmacology of the Diastereoisomers of N-[3-Methyl-1-(2-phenylethyl)4-piperidyl]-N-phenylpropanamide and N-[3-Methyl-1-91methyl-2-phenylethyl)-4-piperidyl]-N-phenylpropanamide, Journal of Medical Chemistry, Mar. 26, 1974, pp. 1047-1051, vol. 17, No. 10, 1974, The American Chemical Society, U.S.A.
V.D. Kiricojevic et al., An Optimized Synthesis of a Key Pharmaceutical Intermediate Methyl 4-[(1-oxopropyl)Phenylamino]Peperidine-4-Carboxylate, Journal of Serbian Chemical Society, Aug. 26, 2002, pp. 793-802, vol. 67, No. 12, The Serbian Chemical Society, Serbia.
Van Daele, P. G. H. et al., Synthetic Analgesics: N-(1-[2-Arylethyl]-4-substtuted 4-Piperidinyl) n-Arylalkanamides, Arzneim-Forsch (Drug Research), vol. 26, Nr. 8, pp. 521-1531 (1976).
Bagley, Jerome R., et al., New 1-(Hheterocyclylalkyl)-4-(propionanilido)-4-Piperidinyl Methyl Ester and Methylene Methyl Ester Analgesics, J. Med. Chem., vol. 34, pp. 827-841 (1991).
Janssens, Frans, Synthetic 1,4-Disubstituted-1,4-dihydro-5H-tetrazol-5-one Derivatives of Fentanyl: Alfentanyl (R 39209), a Potent, Extremely Short-Acting Narcotic Analgesic, J. Med. Chem., vol. 29, pp. 2290-2297 (1986).
Notification of Transmittal of International Search report and Written Opinion for PCT/US2009/063211, Apr. 2009.
International Search report for PCT/US2009/063211, Apr. 2009.
Written Opinion for PCT/US2009/063211, Apr. 2009.

* cited by examiner

*Primary Examiner* — Rita Desai
*Assistant Examiner* — Ben S Michelson
(74) *Attorney, Agent, or Firm* — Banner & Witcoff, Ltd.

(57) ABSTRACT

The present invention relates to a process for the preparation of piperidine derivatives including sufentanil, and their pharmaceutically acceptable salts, such as the citrate salt in which a quaternary ammonium (nosylate) salt of an appropriate piperidine is reacted with a corresponding 4-$NO_2$ sulfonate ester to produce the desired piperidine derivative at a high purity.

7 Claims, No Drawings

METHOD OF MAKING PIPERIDINE DERIVATIVES

CROSS REFERENCE TO RELATED APPLICATIONS

This application claims priority to Provisional application Ser. No. 61/111,118 filed Nov. 4, 2008, the disclosure of which is incorporated herein by reference thereto.

FIELD OF THE INVENTION

The present invention relates to a process for the preparation of piperidine derivatives, including sufentanil, and their pharmaceutically acceptable salts.

BACKGROUND OF THE INVENTION

Sufentanil is a piperidine derivative and is one member of a series of potent fentanyl analogues. Other 4-anilido-piperidines in this series are remifentanil, carfentanil and alfentanil. In general, these materials are characterized by a high analgesic potency, a short duration of action and a relatively good overall safety margin during surgical anesthesia.

Sufentanil, in particular, is considered a powerful analgesic with an excellent safety margin as compared to other narcotic agents. Sufentanil has a high selectivity and affinity (approximately 10 times greater than fentanyl) for "mu" opiate receptors. Unlike fentanyl or morphine, sufentanil produces anesthesia with minimal side-effects. Sufentanil, when used in high doses with 100% oxygen in patients undergoing major surgical procedures has shown excellent cardiovascular stability, maintaining cardiac output and myocardial oxygen balance with minimal changes in heart rate.

Because of its low cardiovascular toxicity, sufentanil has utility as a total intravenous anesthetic for major surgical procedures and finds particular utility for open heart surgery and major operations in patients with severe cardiovascular compromise.

The chemical name for sufentanil is N-[4-(methoxymethyl)-1[2-(2-thienyl)ethyl]-4-piperidinyl]-N-phenylpropanamide. Sufentanil citrate is a white crystalline powder (molecular weight=578.68) that is very soluble in water and most common organic solvents.

Methods of synthesizing sufentanil and related piperidine derivatives are described in the following references: U.S. Pat. Nos. 3,998,834, 4,179,569, 5,489,689 and WO 2008/005423; each of which is incorporated herein by reference in its entirety. There remains a need in the art for improved processes for producing such piperidine derivatives including sufentanil.

SUMMARY OF THE INVENTION

The present invention provides a process for preparing a 4-anilido-piperidine derivative of formula (4):

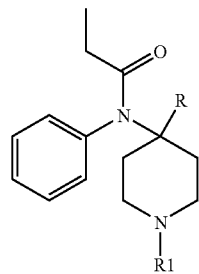

(4)

Where R is either —COOMe or —CH$_2$OMe and where R1 is selected from the following formulae (a), (b), (c), or (d):

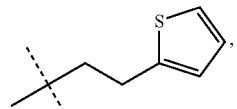

(a)

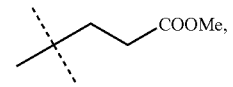

(b)

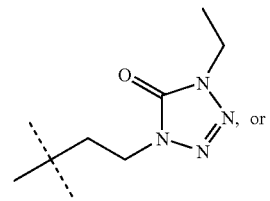

(c)

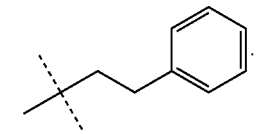

(d)

The present invention particularly relates to a process for producing piperidine derivatives, including sufentanil, remifentanil, alfentanil and carfentanil from a key N-protected intermediate, including the acid addition salts thereof, of the following formula (1):

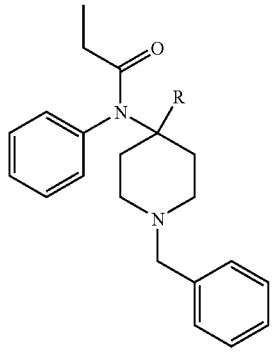

(1)

Where R is either —COOMe or —CH$_2$OMe. Me is simply a shorthanded way to represent a terminal methyl (—CH$_3$) group.

The process involves sequentially debenzylating the intermediate (1), or one of its acid addition salts under suitable conditions, such as catalytic hydrogenation using a palladium on carbon catalyst, and then reacting the deprotected intermediate with nitrobenzenesulfonic acid to produce the piperidine quaternary ammonium (nosylate) salt of formula (2) in high yield:

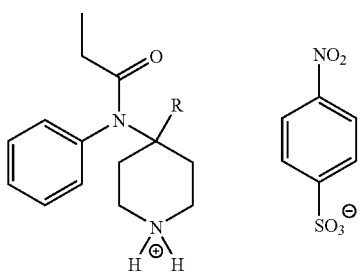

(2)

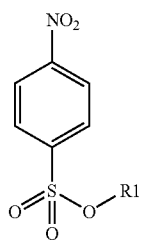

(3)

The piperidine ammonium salt (2) is then reacted with an appropriate 4-NO$_2$ sulfonate ester of formula (3) to produce the desired piperidine derivative:

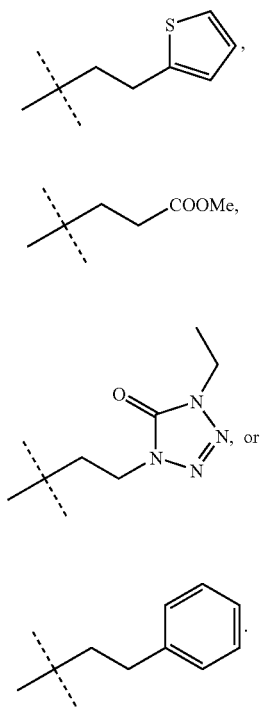

Where R1 is selected from the following formulae (a), (b), (c), or (d):

The 4-NO$_2$ sulfonate ester itself is prepared by reacting the corresponding alcohol, selected from (a1), (b1), (c1), or (d1) with 4-nitrobenzenesulfonyl chloride:

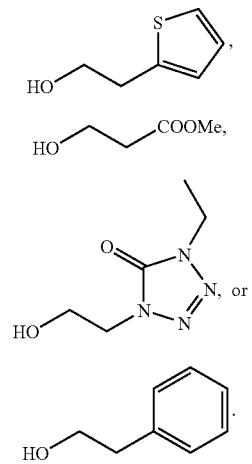

The 4-anilido-piperidine derivative, such as sufentanil, can be isolated as a free base. Alternatively, the free base can be, in turn, formed into a different pharmaceutically acceptable salt, such as a citrate salt, as described in the examples below. Obviously, the so-produced 4-anilido-piperidine derivative also can be isolated by any suitable method.

DETAILED DESCRIPTION OF THE INVENTION

Intermediate (1), and its acid addition salts used as the starting material in connection with the process of the present invention, is a known intermediate used in prior art synthesis approaches for making 4-anilido-piperidine derivatives:

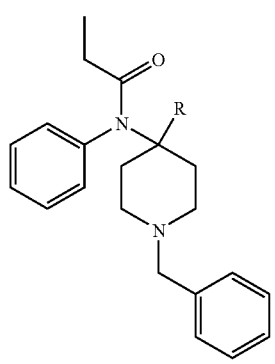

(1)

Where R is either —COOMe or —CH$_2$OMe.

The prior art has described ways of making intermediate (1) where R is —CH$_2$OMe and any way can be used to make this stating material. One suitable approach is described in WO 2008/005423, which starts the synthesis with 1-benzyl-4-piperidone. See examples 1 through 7 of the noted published PCT application, the disclosures of which are incorporated herein by reference. Another approach is identified as Scheme I in U.S. Pat. No. 7,074,935, with reference to U.S. Pat. No. 3,998,834.

The prior art also has described ways of making intermediate (1) where R is —COOMe and any way can be used to make this starting material. One approach is described in V. D. Kiricojević et al., "An optimized Synthesis of a Key Pharmaceutical Intermediate methyl 4-[(1-oxopropyl)phenylamino] piperidine-4-carboxylate," *J. Serb. Chem. Soc.*, Vol. 67(12):

793-802 (2002), which also starts the synthesis with 1-benzyl-4-piperidone. The disclosure of this article also is incorporated herein by reference. Again, any way of making these starting materials can be used for practicing the present invention.

In accordance with the present invention, the benzyl protecting the piperidine nitrogen of intermediate (1) is initially removed. Procedures for debenzylating protected intermediate (1) and its salts, such as by catalytic hydrogenation over a suitable catalyst, generally a palladium on carbon catalyst, are described in the above-noted prior art references as well and thus are well known to those skilled in the art. Any way for effecting the debenzylation reaction is considered to be within the scope of the present invention.

In accordance with the present invention, once the deprotected (debenzylated) intermediate is obtained, it is reacted with nitrobenzenesulfonic acid in a suitable solvent to produce the piperidine quaternary ammonium (nosylate) salt of formula (2) in high yield and purity:

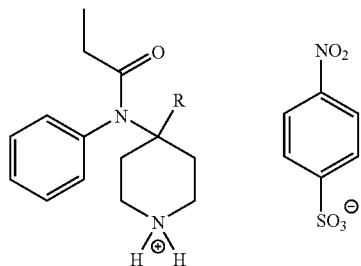
(2)

Solvents for the reaction of intermediate (1) with nitrobenzenesulfonic acid include ethyl acetate, 2-propanol, isopropyl acetate, ethanol, methanol and mixtures thereof. Other solvents can be identified through routine screening practices.

The reaction can be conducted at a temperature between 25° C. and 40° C. and preferably not greater than 50° C. Following recovery of the piperidine quaternary ammonium (nosylate) salt of formula (2), the salt is then reacted with a 4-NO$_2$ benzenesulfonic acid ester of the following formula (3):

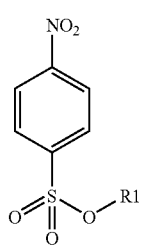
(3)

Where R1 is the moiety appropriate for the desired 4-anilido-piperidine derivative, depending on R in the original starting material.

For example, in the case of sufentanil, R is —CH$_2$OMe and R1 is

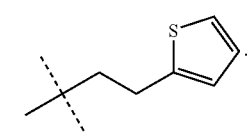

For alfentanil, R is —CH$_2$OMe and R1 is

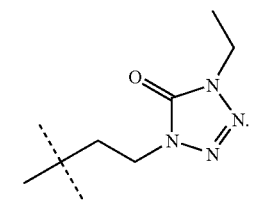

For remifentanil, R is —COOMe and R1 is

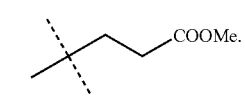

For carfentanil, R is —COOMe and R1 is

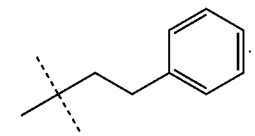

The reaction of the piperidine quaternary ammonium (nosylate) salt of formula (2) with a 4-NO$_2$ benzenesulfonic acid ester of formula (3) can be conducted in ethyl acetate, isopropyl acetate, tetrahydrofuran and other ethers such as t-butyl methyl ether, in triethylamine, or in methylene chloride in the presence of a suitable base such as triethylamine, or ethyl diisopropyl amine. Still other solvent and base combinations can be identified using only routine testing. The reaction proceeds adequately at a temperature in the range of 5° C. to 75° C. to yield the appropriate 4-anilido-piperidine derivative.

The 4-NO$_2$ benzenesulfonic acid ester of formula (3) used to produce the 4-anilido-piperidine derivative is prepared by reacting 4-nitrobenzenesulfonyl chloride with an alcohol selected from (a1), (b1), (c1), or (d1):

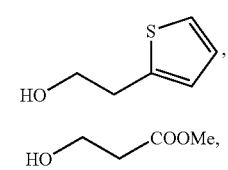
(a1)
(b1)

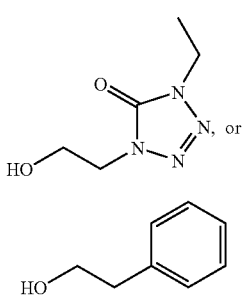

The 2-(2-thienyl)ethanol (alternatively known as 2-thiopheneethanol) (a1) used in the synthesis of the 4-NO$_2$ sulfonate ester for making sufentanil is a well known reagent and is commercially available, such as from Sigma-Aldrich, Inc., St. Louis, Mo., USA.

The methyl ester of 3-hydroxy propionic acid (also known as methyl 3-hydroxy-propanoate) (b1) used in the synthesis of the 4-NO$_2$ sulfonate ester for making remifentanil also is commercially available from a variety of sources such as 3B Scientific Corporation, 1840 Industrial Drive, Suite 160, Libertyville, Ill., 60048; ARVI Fine Organic Chemicals Co. LTD, Davidashen-131-36, Yerevan, Armenia, 375000; Kaneka America LLC, Fine Chemicals Division, 546 Fifth Avenue, 21st Floor, New York, N.Y. 10036; and SinoChemexper Company, 669 Pingxinguan Rd, 1#, Room 402, Shanghai, People's Republic of China, 200072

The 1-ethyl-4-(2-hydroxy-ethyl)-1,4-dihydro-tetrazol-5-one (e1) used in the synthesis of the 4-NO$_2$ sulfonate ester for making alfentanil can be made by reacting 1-ethyl-1H-tetrazol-5(4H)-one with ethylene oxide as shown below. The starting 1-ethyl-1H-tetrazol-5(4H)-one is available from Acros Organics, or from Dynamit Nobel GmBH.

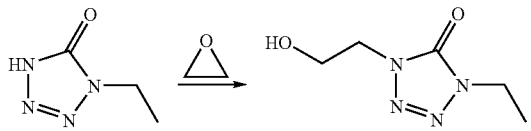

Finally, the 2-phenylethanol (d1) used in the synthesis of the 4-NO$_2$ sulfonate ester for making carfentanil is a well known reagent and is commercially available from Sigma-Aldrich, Inc., St. Louis, Mo., USA.

The reaction between the appropriate alcohol and 4-nitrobenzenesulfonyl chloride is conducted in methylene chloride (dichloromethane), ethyl acetate, isopropyl acetate and ethers, in the presence of an organic base such as triethylamine and a catalysts such as 4-dimethylaminopyridine. Other solvents, organic bases and catalysts can be identified by those skilled in the art using routine testing. The reaction is conveniently performed at a temperature of less than 20° C., and usually between 0° C. and 15° C. Purification of the resulting 4-nitrobenzene sulfonate ester can be accomplished simply by precipitating the product solids from solution. As illustrated in Example 2 below, purified 4-nitrobenzene sulfonate ester can be precipitated from a mixture of ethyl acetate and n-heptane. The purified ester of formula (3) then is reacted with the piperidine quaternary ammonium (nosylate) salt of formula (2) to yield the desired 4-anilido-piperidine derivative.

The desired 4-anilido-piperidine derivative can be isolated as the free base, or as an HCl salt, and then converted to a free base. The free base then can be converted into another pharmaceutically acceptable salt by any suitable method, such as a citrate salt as exemplified for sufentanil in one of the following examples. Suitable pharmaceutically salts potentially include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, laurylsulphonate salts, and others.

The invention is further illustrated by the following examples, which are not to be construed as limiting.

Example 1

4-[(1-oxopropyl)phenylamino]-4-methoxymethyl piperidine nosylate

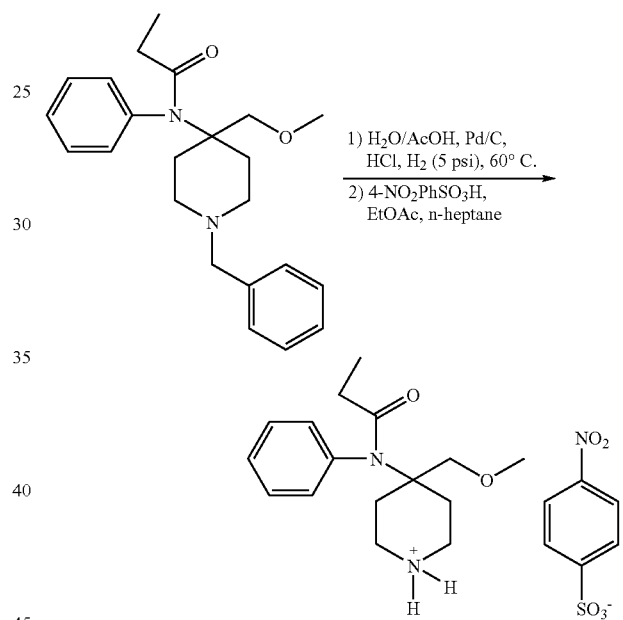

In a 2.0 L, 3-necked round bottom flask equipped with magnetic stirrer, temperature probe and a gas reservoir at atmospheric pressure, intermediate (1) (154.0 g; 0.42 moles; 1 equivalent) was dissolved in 1037 mL of a water-acetic acid mixture (H$_2$O:AcOH mixture of 5:4 parts by volume; and containing 130 mL of concentrated hydrochloric acid. (12 M HCl).

Then, 22.4 g (50% wet) of 10% Pd/C was charged into the flask. After evacuative purging of the gas space of the flask with nitrogen/vacuum (3 times), followed by evacuative purging of the gas space of the flask with hydrogen/vacuum (3 times), the reaction mixture was stirred for 36 hours at 60° C. with a H$_2$ reservoir at atmospheric pressure in place.

Thereafter, the reaction mixture was filtered to remove the catalyst and, the catalyst was washed with water (1000 mL). The wash water was combined with the filtrate. The combination filtrate and wash water then was cooled in an ice-bath and a sufficient amount of a 50 wt. % NaOH solution was added to the reaction mixture to adjust the pH to 13 (as measured by indicator paper), while keeping the temperature of the reaction mixture below 30° C.

The pH-adjusted reaction mixture was extracted with methyl tert-butyl ether (MTBE) (2 times using 1000 mL each time). The aqueous phase was discarded and the combined MTBE extracts (i.e., the organic phase) were dried (Na$_2$SO$_4$), filtered and then residual solvent was removed under reduced pressure to yield an oily product (110 g; 94.8% yield). HPLC analysis gave 94% purity.

2.10 g (not dried weight) of the crude oil was transferred to a 50 mL, 3 necked flask. The flask was charged with ethyl acetate (10 mL) followed by a solution of 4-nitrobenzene-sulfonic acid (1.52 g of nitrobenzenesulfonic acid dissolved in a mixture of 15 ml ethyl acetate and 5 ml 2-propanol). The reaction mixture was warmed to 38° C., yielding a clear yellow solution. The resultant reaction mixture was allowed to warm to room temperature with stirring. In order to recover the desired product, the reaction mixture was cooled in an ice-bath to 5° C. and 4 mL of n-heptane was added, causing some solids to precipitate.

The precipitated solids were filtered, and then washed with n-heptane to yield 2.90 g of the desired 4-[(1-oxopropyl)phenylamino]-4-methoxymethyl piperidine nosylate product (80.5% yield; 97.7% HPLC purity).

1.30 g (not dried weight) of the salt then was transferred to a 50 mL, 3 necked flask, to which 10 mL of ethyl acetate was added. The mixture was heated to 50° C. to completely dissolve the solids. As the solution slowly cooled with stirring, the reaction mixture became cloudy at 42° C. The mixture then was cooled in an ice-bath to 5° C. and held at that temperature for 1 hour causing solids to form. The solids were filtered and washed with n-heptane yielding 1.0 g of further purified 4-[(1-oxopropyl)phenylamino]-4-methoxymethyl piperidine nosylate product (78% yield; 99.4% HPLC purity).

Example 1A

4-[(1-oxopropyl)phenylamino]-4-methoxymethyl piperidine nosylate

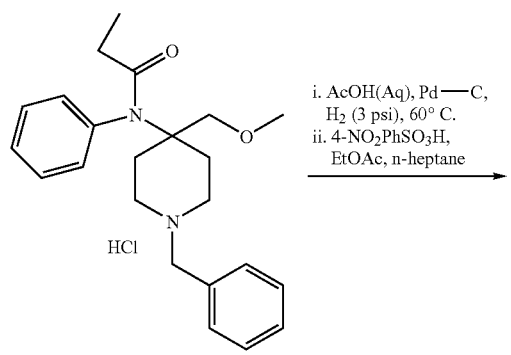

In a suitably sized glass pressure vessel (e.g., a 2.0 L, 3-necked round bottom flask equipped with magnetic stirrer, temperature probe and a gas reservoir at atmospheric pressure), HCl salt of intermediate (1) (100.0 g) is dissolved in 400 mL of a water-acetic acid mixture (H$_2$O:AcOH mixture of 1:1 parts by volume).

Then, 10 g (wet) of 10% Pd/C is charged into the flask. After evacuative purging of the gas space of the flask with nitrogen/vacuum (3 times), followed by evacuative purging of the gas space of the flask with hydrogen (~5 psig)/vacuum (3 times), the reaction mixture is stirred for at least 12 hours at 60° C.±5° C. with a H$_2$ reservoir at about 2-3 psig until substantially all of the intermediate salt has been consumed.

Thereafter, the reaction mixture is filtered to remove the catalyst and, the catalyst is washed with water (1000 mL). The wash water is combined with the filtrate. The combination filtrate and wash water then are cooled to less than 5° C. and a sufficient amount of a 50 wt. % NaOH solution is added to the reaction mixture to adjust the pH to greater than 12, while keeping the temperature of the reaction mixture below 30° C.

The pH-adjusted reaction mixture is extracted with ethyl acetate (4 times using 600 mL each time). The aqueous phase is discarded and the combined ethyl acetate extracts (i.e., the organic phase) are passed through a carbon/Cf UTE® diatomaceous earth bed and the bed is washed with an additional 500 ml of ethyl acetate. Residual solvent is removed under reduced pressure to yield an oily product (55.90 g; 82% yield; expected purity 99.0%).

55.9 g of the oily product is transferred to a suitably sized flask. The flask is charged with ethyl acetate (278.7 mL) with mixing. In a separate suitably sized flask, a solution of 4-nitrobenzenesulfonic acid (54.49 g) dissolved in a mixture of 222.6 ml ethyl acetate and 55.7 ml 2-propanol is prepared. The solution is added through a polish filter to the flask containing the solution of the oily product. A slight exotherm should be observed as the 4-nitrobenzenesulfonic acid solution is added and the reaction mixture is warmed to at least 40° C., but not greater than 50° C. Thereafter, 552.5 ml of heptane is added to the reaction mixture, which then is cooled to 15° C.±5° C., held for 15 minutes and then cooled to 0° C.±5° C. and held for at least an additional 60 minutes causing some solids to precipitate.

The precipitated solids are filtered (using a Buchner filter), washed twice with n-heptane (each 336.8 ml) and then dried in a vacuum oven at 50° C. to yield 93.9 g of the desired 4-[(1-oxopropyl)phenylamino]-4-methoxymethyl piperidine nosylate product (expected 97% yield; expected 99.97% purity).

Example 2

2-(2-thiophenylethyl) 4-nitro-benzene sulfonate (4-NO$_2$-benzene sulfonate ester of 2-thiopheneethanol)

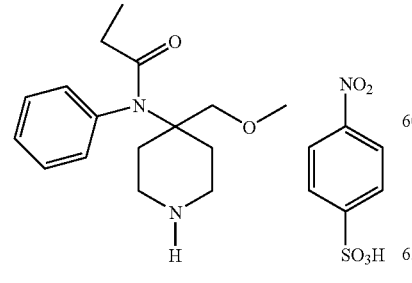

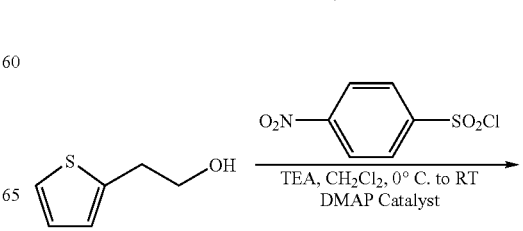

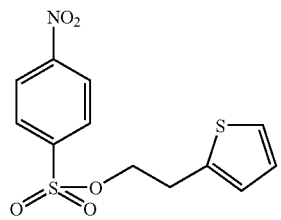

2-thiopheneethanol (200.0 g; 1.56 moles; 1 equivalent), triethylamine (283 mL; 2.0 moles; 1.3 equivalents), 4-dimethylaminopyridine (DMAP) catalyst (2 g; 0.02 moles; 0.01 equivalent) and methylene chloride (1500 mL) were added to a 5.0 L, 4-necked round bottom flask equipped with overhead stirrer, temperature probe, $N_2$ inlet and addition funnel to form a reaction mixture.

The reaction mixture was cooled to 10° C. and 4-nitrobenzenesulfonyl chloride (415 g; 1.87 moles; 1.20 equivalents) was added as a slurry in methylene chloride (1000 mL) over a period of 2.0 hours, while keeping the reaction temperature below 15° C. Thereafter, under constant stirring, the reaction mixture was allowed to warm for 4 hours to room temperature. Yellow material precipitated from the solution, which was diluted with water (1000 mL) and stirred for 10 minutes. Two phases separated and additional water (1000 mL) was added and the mixture was stirred for 10 more minutes. The two phases that formed were separated and solvent was removed from the organic phase under reduced pressure to provide an orange solid as a crude 2-(2-thiophenylethyl) 4-nitro-benzene sulfonate product (570 g; 116% wet yield; HPLC purity 93.8%).

To purify the crude product, 10 g of the solids were mixed with ethyl acetate (50 mL) and n-heptane (200 mL) and the mixture was heated at 48° C. to yield an almost clear solution (some non-dissolved dark solids were observed and were separated from the clear solution). The solution was allowed to warm to room temperature without stirring. Then, the solution was cooled in an ice-bath to 5° C. and held for 30 minutes. The light yellow crystals that formed were filtered and washed with n-heptane (30 mL) to yield 6.05 g (dried weight) of 2-(2-thiophenylethyl) 4-nitro-benzene sulfonate product (60% yield; 99.9% HPLC purity).

Example 3

N-[4-(methoxymethyl)-1-[2-(2-thienyl)ethyl]-4-piperidinyl]-N-phenylpropanamide (Sufentanil)

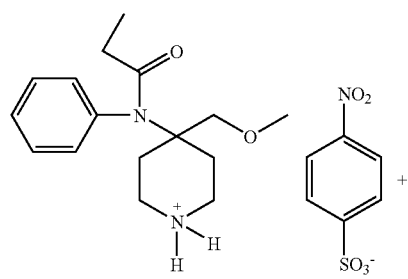

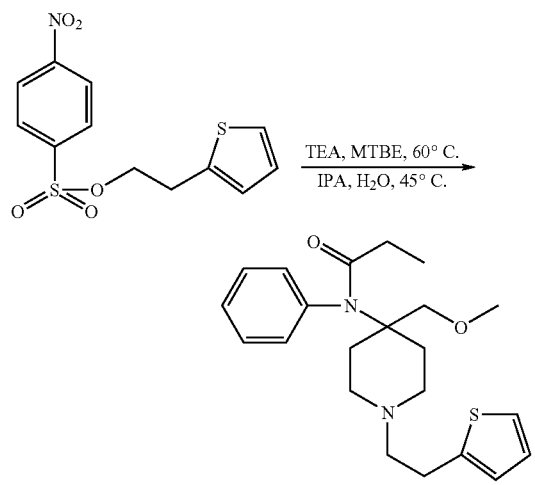

To a jacketed glass reactor with stirring, nitrogen blanket, internal temperature recorder, and reflux capabilities was charged 4-[(1-oxopropyl)phenylamino]-4-methoxymethyl piperidine nosylate (100.0 g, 21 mmol), 2-(2-thiophenylethyl) 4-nitro-benzene sulfonate (71.9 g, 23 mmol), tert-butyl methyl ether (MTBE, 222 g, 300 mL), and triethylamine (TEA, 436 g, 4.3 mol). The reaction mixture was warmed to 60±5° C. As the reaction progressed, a slurry was formed. After 5 hours, the system was cooled and charged with MTBE (296 g, 400 mL). This diluted system was washed sequentially with water (400 mL), 5% aqueous sodium bicarbonate (400 mL), water (400 mL), and water (400 mL). The solvent was removed by distillation and replaced with iso-propanol (394 g, 500 mL). The system was warmed to give a clear solution at 45° C. Water (800 g, 800 mL) was added to give a turbid system at 45° C. The hazy slurry was cooled slowly to ambient temperature, then further cooled to 5° C., and held at that temperature for approximately 15 hours. The resultant slurry was filtered and washed with 40% aqueous iso-propanol to provide white crystals. The solids were dried to constant weight under vacuum at 55° C. This process provided 67.5 g (84 mol %) of sufentanil as a white solid, purity over 99% by HPLC.

Example 3A

N-[4-(methoxymethyl)-1-[2-(2-thienyl)ethyl]-4-piperidinyl]-N-phenylpropanamide (Sufentanil)

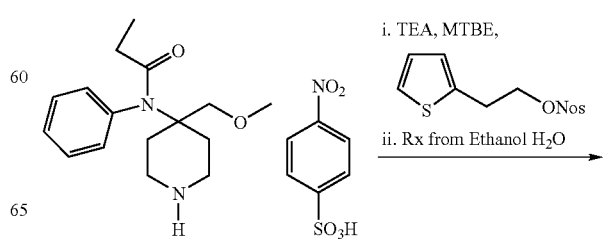

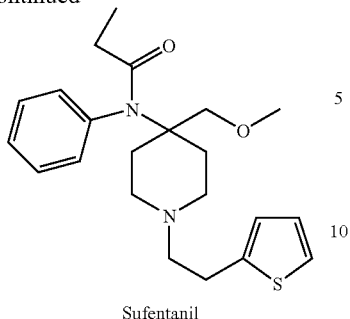

Sufentanil

To a suitably sized reaction flask (e.g., a jacketed glass reactor with stirring, nitrogen blanket, internal temperature recorder, and reflux capabilities) is charged 4-[(1-oxopropyl)phenylamino]-4-methoxymethyl piperidine nosylate (100.0 g), 2-(2-thiophenylethyl) 4-nitro-benzene sulfonate (79.2 g), tert-butyl methyl ether (MTBE, 333 mL), and triethylamine (TEA, 666 mL). The reaction mixture is warmed to 55°±5° C. and allowed to react at that temperature for not less than 24 hours. As the reaction progresses, a slurry is formed. The extent of the reaction can be followed by HPLC until most of the initial reactants are consumed. At that point, the reaction mixture is cooled to 20°±5° C. and charged with MTBE (400 mL) and water (400 mL). The diluted slurry is mixed for at least 10 minutes and then aqueous and organic phases are allowed to separate in a separatory funnel. The aqueous phase is discarded and then the organic phase is washed with water two additional times. Carbon (20 g) is then added to the resultant organic phase, mixed for at least 10 minutes and the carbon is filtered from the organic phase through a CELITE® diatomaceous earth bed. The CELITE® diatomaceous earth bed is washed with 200 ml of MTBE, the organic phases are combined and then solvent exchanged with ethanol under vacuum distillation conditions (by concentrating the organic phase to minimum stir volume three times and thereafter adding 400 mL of ethanol following each step of concentrating). The final volume should be about 600 mL. The solution is warmed to 45°±5° C. and then water (834 mL) is added slowly to give a turbid system. The hazy slurry is cooled slowly to 5°±5° C., and held at that temperature for at least 16 hours. The resultant slurry is filtered, washed with 30% aqueous ethanol and then dried in a vacuum oven at 50° C. to yield 67.9 g of the desired sufentanil product (expected yield 84%; expected purity 99.7%).

Example 4

Sufentanil Citrate

The sufentanil obtained in Example 3 can be converted to the citrate salt as follows. Sufentanil (9.81 g, 0.025 mol) is suspended in isopropanol (125 mL), and warmed to 40-45° C. with stirring to get a light yellow clear solution. To this solution, a solution of citric acid (4.87 g, 0.025 mol) in isopropyl alcohol (IPA) (34.0 mL) is added over a period of 5 minutes at a temperature of 45° C. to yield a clear solution. The resulting mixture is allowed to cool to room temperature forming a white precipitate which is filtered. The white filter cake is washed with IPA (2×10 mL) and the washed solids are air dried to get a white powder (14.9 g) of the citrate salt.

The present invention has been described with reference to specific embodiments. However, this application is intended to cover those changes and substitutions that may be made by those skilled in the art without departing from the spirit and the scope of the invention. Unless otherwise specifically indicated, all percentages are by weight. Throughout the specification and in the claims the term "about" is intended to encompass + or −5% and preferably is only about + or −2%.

What is claimed is:

1. A method of making a 4-anilido-piperidine derivative of formula (4) comprising:

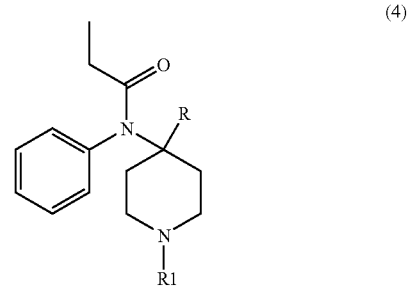

(4)

reacting a piperidine ammonium salt of formula (2)

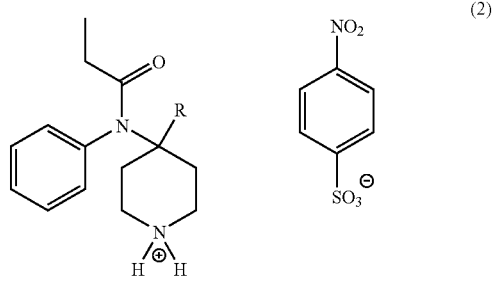

(2)

with a 4-NO$_2$ sulfonate ester of formula (3)

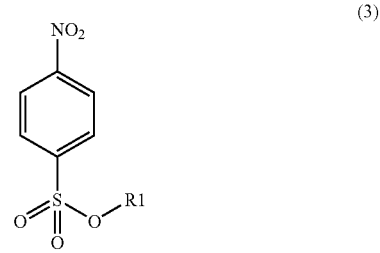

(3)

where R is selected from —COOMe or —CH$_2$OMe, and where R1 is selected from the following formulae (a), (b), (c), or (d):

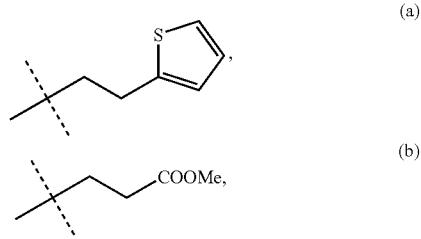

15

-continued

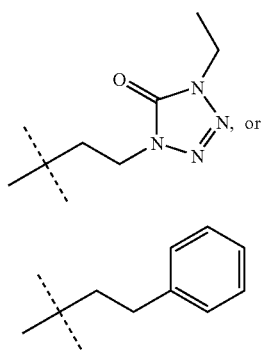
(c)

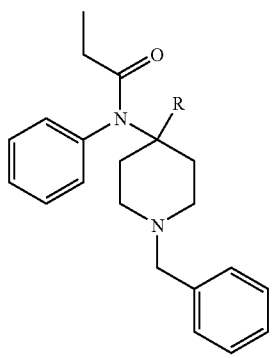
(d)

to produce the 4-anilido-piperidine derivative.

2. The method of claim 1 wherein the 4-NO$_2$ sulfonate ester of formula (3) is prepared by reacting an alcohol selected from formula (a1), (b1), (c1), or (d1) with 4-nitrobenzenesulfonyl chloride:

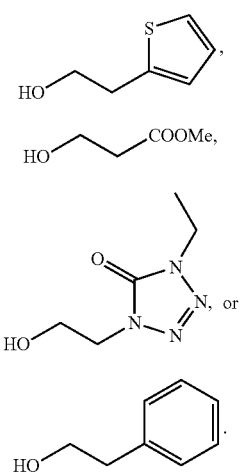

(a1)

(b1)

(c1)

(d1)

3. The method of claim 1 wherein the piperidine ammonium salt of formula (2) is prepared by debenzylating the intermediate of following formula (1), or a salt thereof:

(1)

and then reacting the deprotected intermediate with nitrobenzenesulfonic acid.

4. The method of claim 1 for making sufentanil wherein a piperidine ammonium salt of formula (2B)

16

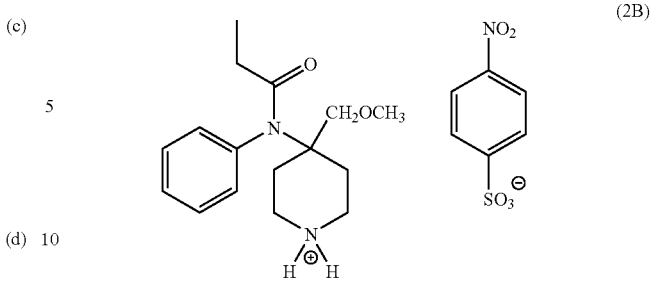
(2B)

is reacted with a 4-NO$_2$ sulfonate ester of formula (3B)

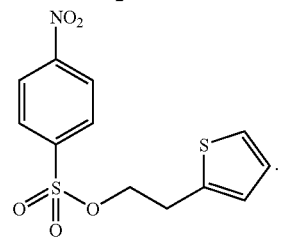
(3B)

5. The method of claim 4 wherein the 4-NO$_2$ sulfonate ester of formula (3B) is prepared by reacting 2-(2-thienyl)ethanol with 4-nitrobenzenesulfonyl chloride.

6. The method of claim 4 wherein the wherein the piperidine ammonium salt of formula (2B) is prepared by debenzylating an intermediate of following formula (1B), or a salt thereof:

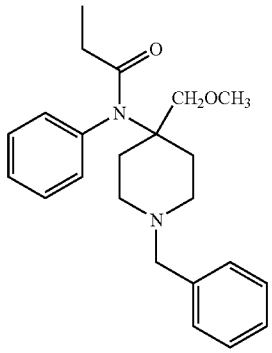
(1B)

and then contacting the deprotected intermediate with nitrobenzenesulfonic acid.

7. The method of claim 5 wherein the wherein the piperidine ammonium salt of formula (2B) is prepared by debenzylating an intermediate of following formula (1B) or a salt thereof:

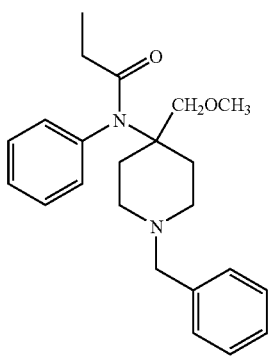
(1B)

and then reacting the deprotected intermediate with nitrobenzenesulfonic acid.

* * * * *